United States Patent [19]

Grollier

[11] Patent Number: 5,021,067
[45] Date of Patent: Jun. 4, 1991

[54] COMPOSITION FOR DYEING KERATINOUS FIBRES EMPLOYING AN INDOLE DYE AND AT LEAST ONE PARA-PHENYLENEDIAMINE DISUBSTITUTED ON ONE OF THE AMINO GROUPS AND PROCESS EMPLOYING IT

[75] Inventor: Jean F. Grollier, Paris, France

[73] Assignee: L'Oreal, Paris, France

[21] Appl. No.: 307,792

[22] Filed: Feb. 8, 1989

[30] Foreign Application Priority Data

Feb. 8, 1988 [LU] Luxembourg ............... 87128

[51] Int. Cl.$^5$ .................................. A61K 7/13
[52] U.S. Cl. ........................................ 8/409; 8/423; 8/410; 8/421
[58] Field of Search ............... 8/406, 407, 408, 410, 8/415, 423

[56] References Cited

U.S. PATENT DOCUMENTS

| 4,314,810 | 2/1982 | Fourcadier et al. | 8/429 |
| 4,776,857 | 10/1988 | Camol et al. | 8/405 |
| 4,804,385 | 2/1989 | Grollier et al. | 8/406 |
| 4,808,190 | 2/1989 | Grollier et al. | 8/406 |
| 4,822,375 | 4/1989 | Lang et al. | 8/408 |

FOREIGN PATENT DOCUMENTS 3031709 4/1982 Fed. Rep. of Germany .......... 8/406

Primary Examiner—Paul Lieberman
Assistant Examiner—J. E. Darland
Attorney, Agent, or Firm—Cushman, Darby & Cushman

[57] ABSTRACT

Dyeing composition for keratinous fibres, and especially for human keratinous fibres, characterized in that it contains, in a cosmetically acceptable aqueous medium:

(a) an indole dye, and
(b) a para-phenylenediamine disubstituted on one of the amino groups, corresponding to the formula:

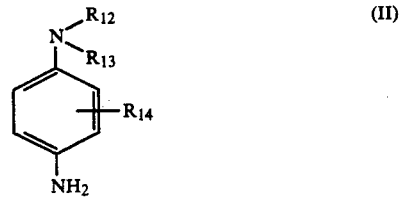

(II)

in which $R_{12}$ and $R_{13}$, which may be identical or different, denote a $C_1$–$C_4$ alkyl group; a $C_2$–$C_4$ hydroxyalkyl group; or a $C_1$–$C_4$ alkyl group substituted with an $SO_3H$ group, or with a mesylamino or acetylamino group, or with a $C_1$–$C_4$ alkoxy group, or with a carbamyl group substituted or otherwise with one or two $C_1$–$C_4$ alkyl groups, or with a heterocyclic amine; it also being possible for $R_{12}$ and $R_{13}$ to form, with the nitrogen atom to which they are attached, a 4- to 6-membered heterocycle; and $R_{14}$ denotes hydrogen or a $C_1$–$C_4$ alkyl, $C_1$–$C_4$ alkoxy or halogen group; or their cosmetically acceptable addition salts with an acid.

17 Claims, No Drawings

COMPOSITION FOR DYEING KERATINOUS FIBRES EMPLOYING AN INDOLE DYE AND AT LEAST ONE PARA-PHENYLENEDIAMINE DISUBSTITUTED ON ONE OF THE AMINO GROUPS AND PROCESS EMPLOYING IT

The present invention relates to new compositions for dyeing keratinous fibers, and more especially human keratinous fibers such as the hair, containing an indole dye in combination with at least one para-phenylenediamine disubstituted on one of the amino groups, as well as to the processes employing these compositions.

The color of the hair, the skin and hairs of human origin originates mainly from the melanin pigments secreted by the melanocytes.

These pigments, of natural origin, comprise, in particular, pigments known as eumelanins.

Their natural biosynthesis takes place in several stages by polymerization of the oxidation products of an amino acid, namely tyrosine, and one of these oxidation products is 5,6-dihydroxyindole which, in turn, polymerizes to eumelanin.

The proposal has already been made in the past to dye human hair with 5,6-dihydroxyindole or indole dyes. It is known that 5,6-dihydroxyindole enables, in particular, progressive dyeing of the hair to be carried out, that is to say makes it possible to obtain from light hues, by one application of the product, to dark tints, by superposition of applications.

The dyeing takes place slowly, however, and, to accelerate the formation of the melanin pigment and obtain dark hues more rapidly, different processes have already been described, such as those described in French Patent Nos. 1,133,594 and 1,166,172, employing two stages and oxidizing agents such as hydrogen peroxide or catalytic oxidizing agents of a metallic nature.

The applicant has just discovered, and this forms the subject of the invention, that, by using an aqueous solution of an indole dye containing at least one paraphenylenediamine disubstituted on one of the amino groups, or its addition salts, it was possible to obtain very rapidly a progressive dyeing of the hair from blond to black hues.

The applicant found, in addition, that, with the composition according to the invention, the hair was more rapidly dyed black or dyed in dark tints, compared with the traditional process using only the indole dye by way of a dye.

The compositions according to the invention permit a progressive dyeing of human hair in the ambient air.

The subject of the invention is hence dyeing compositions for keratinous fibers, and especially for human keratinous fibers such as human hair, containing, by way of dyes, an indole dye and at least one paraphenylenediamine disubstituted on one of the amino groups.

Another subject of the invention consists of the dyeing process employing such a composition.

Other subjects of the invention will become apparent on reading the description and the examples which follow.

The dyeing composition according to the invention is essentially characterized in that it contains, in an aqueous medium suitable for dyeing, an indole dye and at least one para-phenylenediamine disubstituted on one of the amino groups, or its addition salts with an acid.

The indole dye corresponds to the formula:

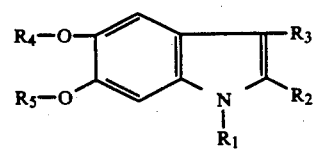

(I)

in which:

$R_1$ denotes a hydrogen atom, a lower alkyl group or a group $-SiR_6R_7R_8$;

$R_2$ and $R_3$, which may be identical or different, denote a hydrogen atom or alternatively a lower alkyl group, a carboxyl group, a lower alkoxycarbonyl group or a group $-COOSiR_6R_7R_8$;

$R_4$ and $R_5$, which may be identical or different, denote a hydrogen atom, a $C_1-C_{20}$ linear or branched alkyl group, a formyl group, a linear or branched $C_2-C_{20}$ acyl group, a linear or branched $C_3-C_{20}$ alkenoyl group, a group $-SiR_6R_7R_8$, a group $-P(O)(OR_9)_2$, or a group $-SO_2OR_9$, or alternatively $R_4$ and $R_5$, together with the oxygen atoms to which they are attached, from a ring optionally containing a carbonyl group, a methylene group, a thiocarbonyl group or a group: $>P(O)OR_9$, or alternatively $>CR_{10}R_{11}$;

$R_9$ and $R_{10}$ denotes a hydrogen atom or a lower alkyl group, $R_{11}$ denoting a lower alkoxy group or a mono- or dialkylamino group, and $R_6$, $R_7$ and $R_8$, which may be identical or different, denoting linear or branched lower alkyl groups, and the addition salts with inorganic or organic acids, as well as the corresponding salts of alkali metals, alkaline earth metals or amines.

The lower alkyl or alkoxy radicals preferably denote $C_1-C_6$ radicals.

Among preferred compounds of the invention, there will be mentioned 5,6-dihydroxyindole, 2-methyl-5,6-dihydroxyindole, 5-methoxy-6-hydroxyindole, (5 or 6)-acetoxy-(6 or 5)-hydroxyindole or 2-carboxy-5,6-dihydroxyindole, 3-methyl-5,6-dihydroxyindole, 2,3-dimethyl-5,6-dihydroxyindole and their salts.

5,6-dihydroxyindole is especially preferred; it is used as it is or in one of its protected forms such as, for example the diacetate.

The para-phenylenediamines disubstituted on one of the amino groups which are more especially usable according to the invention correspond to the formula:

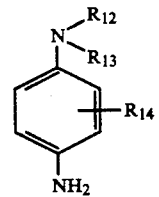

(II)

in which $R_{12}$ and $R_{13}$, which may be identical or different, denote a $C_1-C_4$ lower alkyl group; a $C_2-C_4$ lower hydroxyalkyl group; or a $C_1-C_4$ alkyl group substituted with an $SO_3H$ group, or with a mesylamino or acetylamino group, or with a $C_1-C_4$ alkoxy group, or with a carbamyl group substituted or otherwise with one or two $C_1-C_4$ alkyl groups, or with a heterocyclic amine, it also being possible for $R_{12}$ and $R_{13}$ to form, with the nitrogen atom to which they are attached, a 4- to 6-membered heterocycle and especially a piperidino group;

$R_{14}$, in position 2- or 3, denotes hydrogen or a $C_1$–$C_4$ alkyl, $C_1$–$C_4$ alkoxy or halogen group;

as well as their cosmetically acceptable salts.

Especially preferred compounds corresponding to the formula (II) are those in which $R_{12}$ and $R_{13}$, which may be identical or different, denote a methyl or ethyl or hydroxyethyl group, an ethyl group substituted with a mesylamino, acetylamino, $SO_3H$ or methoxy radical, or with a heterocyclic amine such as piperidine, or a methyl group substituted with a carbamyl or diethylcarbamyl radical, and $R_{14}$ preferably denotes hydrogen or methyl or ethyl, and their salts.

The salts are preferably chosen from hydrochlorides, sulphates, tartrates, etc.

Preferred compounds are chosen, in particular, from N-ethyl-N-(2-hydroxyethyl)-para-phenylenediamine, the sulphate and hydrochloride, N,N-bis(2-hydroxyethyl)-para-phenylenediamine and its salts, N-ethyl-N-(2-piperidinoethyl)-para-phenylenediamine and its trihydrochloride, N-ethyl-N-(carbamylmethyl)para-phenylenediamine, N-ethyl-N-[2-(mesylamino)ethyl]-para-phenylenediamine and its sulphates, and 2-methyl-N,N-dimethyl-para-phenylenediamine and its salts, such as the dihydrochloride.

The most especially preferred compounds of formula (II) are chosen from N,N-bis(2-hydroxyethyl)-para-phenylenediamine and its addition salts such as, for example, the sulphate, hydrochloride and tartrate.

The para-phenylenediamines disubstituted on one of the nitrogen atoms, corresponding to the formula (II), are preferably used in the compositions according to the invention in proportions of between 0.05 and 1% by weight, especially between 0.1 and 0.7% by weight, relative to the total weight of the composition.

The indole dye is preferably used in the composition according to the invention in proportions of between 0.1 and 5% by weight, and preferably between 0.2 and 2% by weight, relative to the total weight of the composition.

In a preferred embodiment, the compositions according to the invention contain other dyes, and in particular so-called "rapid" oxidation dyes, that is to say molecules having a benzene structure, dye precursors, capable of generating the colored compounds by simple oxidation in the air during the exposure time on the hair, generally less than 1 hour, and in the absence of another oxidizing agent.

These "rapid" oxidation dyes are more especially chosen from trihydroxylated derivatives of benzene, and more especially 1,2,4-trihydroxybenzene, or their protected 2,4,5-trihydroxytoluene form such as the triacetate.

According to the invention, these "rapid" oxidation dyes are used in proportions of between 0.02 and 1%, and preferably between 0.05 and 0.3%, by weight relative to the total weight of the composition.

An especially preferred embodiment of the invention consists of a composition containing, in a cosmetically acceptable medium suitable for dyeing, the indole dye, N,N-bis(2-hydroxyethyl)-para-phenylenediamine or one of its salts and 1,2,4-trihydroxybenzene or its triacetate, in sufficient proportions, and preferably those stated above, for dyeing the hair.

The aqueous medium suitable for dyeing has a pH which can vary between 4 and 11, and preferably between 6 and 9. It is adjusted to the desired value using alkalinizing or acidifying agents which are known per se in cosmetics.

The aqueous medium can contain, in addition, cosmetically acceptable solvents in proportions by weight which can range up to 30% relative to the total weight of the composition, and which are chosen more especially from lower alcohols such as ethyl alcohol, propyl alcohol or isopropyl alcohol and tert-butyl alcohol; glycols such as ethylene glycol and propylene glycol; glycol ethers such as ethylene glycol monomethyl, monoethyl and monobutyl ethers, ethylene glycol monoethyl ether acetate, propylene glycol monomethyl ether and dipropylene glycol monomethyl ether; and methyl lactate. Especially preferred solvents consist of ethyl alcohol, propylene glycol monobutylether of ethyleneglycol.

These compositions can assume the form of thickened or unthickened lotions, a gel or an aerosol foam, and can contain adjuvants which are well known in hair dyeing for this type of application, such as plasticizing agents, antioxidant agents, thickening agents, conditioning agents such as cationic polymers and cationic surfactant agents; they can also contain anionic, nonionic or amphoteric surfactant agents, as well as silicones, in particular volatile silicones.

The thickening agents are chosen, more especially, from sodium aliginate, gum arabic, guar or carob gum, heterobiopolysaccharides such as xanthan gum, cellulose derivatives such as methylcellulose, hydroxyethylcellulose, hydroxymethylcellulose, hydroxypropylcellulose and carboxymethylcellulose, and various polymers having thickening functions such as acrylic acid derivatives. It is also possible to use inorganic thickening agents such as bentonite.

These thickening agents are preferably present in proportions of between 0.1 and 5% by weight, and especially between 0.5 and 3% by weight, relative to the total weight of the composition.

The compositions according to the invention preferably contain antioxidant agents, in sufficient proportions for avoiding premature oxidation of the dyes, and preferably between 0.03 and 1% by weight. They are chosen, in particular, from sulphites, hydrosulphites and ascorbic acid.

An embodiment of the invention can also consist in storing the compositions in separate compartments, where appropriate protected from the air, and in carrying out the mixing of the different constituents at the time of use.

The process for dyeing kerationous fibers, and especially human hair, consists in applying on the said fibers at least one composition as defined above, for sufficient time for developing a coloration in the air.

According to a preferred embodiment, the composition is applied several times successively, and it is found that the tint obtained becomes increasingly dark, this also being known as "progressive" dyeing.

The application is followed, after an exposure time of 5 to 50 minutes, by a rinse, optional shampooing, a further rinse and drying.

The examples which follow are designed to illustrate the invention, no limitation of the latter being implied.

EXAMPLE 1

The dyeing of natural grey hair containing 90% of white hair is performed by applying the following composition on the hair:

| | |
|---|---|
| 5,6-Dihydroxyindole | 0.21 g |

| | |
|---|---|
| N,N-Bis(2-hydroxyethyl)-p-phenylenediamine sulphate | 0.41 g |
| Sodium sulphite | 0.03 g |
| Monoethanolamine | 1.50 g |
| Sulphuric acid qs | pH 8 |
| Water qs | 100.00 g |

The composition is left in place for 10 minutes. Conventional shampooing is performed and the hair is then dried in the air.

After one application, the coloration is assessed: it is a stronger and more natural blond coloration than that obtained with a composition containing only 5,6-dihydroxyindole or only N,N-bis(2-hydroxyethyl)-p-phenylenediamine sulphate.

After four successive applications of this composition on the hair, the latter is dyed a bluish light chestnut brown, whereas four applications of the compositions containing only 5,6-dihydroxyindole dye the hair a dark ash-blond and four applications of the composition containing only N,N-bis(2-hydorxyethyl)-p-phenylenediamine sulphate dye the hair an extremely light blond.

EXAMPLE 2

The dyeing of permanent-waved grey hair containing 90% of white hair is performed by applying the following composition on the hair:

| | |
|---|---|
| 5,6-Dihydroxyindole | 0.21 g |
| N,N-bis(2-hydroxyethyl)-p-phenylenediamine sulphate | 0.41 g |
| 1,2,4-Trihydroxybenzene | 0.17 g |
| Sodium sulphite | 0.03 g |
| Monoethanolamine | 1.50 g |
| Sulphuric acid qs | pH 8 |
| Water qs | 100.00 g |

The composition is left in place for 10 minutes. Conventional shampooing is performed, and the hair is then dried in the air.

After four applications of the composition according to the invention, it is found that the hair has a natural black coloration, whereas hair treated with a composition containing only 5,6-dihydorxyindole has a dark ash-blond coloration and hair dyed with the composition containing 1,2,4-trihydroxybenzene is pearly blond.

EXAMPLE 3

| | |
|---|---|
| 5,6-Dihydroxyindole | 0.25 g |
| N-Ethyl-N-carbamylmethyl-para-phenylenediamine | 0.35 g |
| 2,4,5-Trihydroxytoluene | 0.20 g |
| Ethanol | 12.0 g |
| Hydroxyethylcellulose sold by the company Aqualon under the name Natrosol 250 HHR | 1.5 g |
| Preservative | 0.4 g |
| Triethanolamine qs | pH 8 |
| Demineralized water qs | 100.00 g |

Natural grey hair containing 90% of white hair is dyed by applying this composition for 20 minutes. The hair is rinsed, shampooing is performed and the hair is dried. After three applications, hair colored a purple-violet light chestnut brown hue is obtained, while three applications of each of the dyes in the same vehicle lead, respectively, to the following hues:

5,6-dihydroxyindole: dark ash-blond;
N-ethyl-N-carbamylmethyl-para-phenylenediamine: does not dye;
2,4,5-trihydroxytoluene: orange extremely light blond.

EXAMPLE 4

| | |
|---|---|
| 2-Methyl-5,6-dihydroxyindole hydrobromide | 0.6 g |
| N-N-Bis (2-hydroxyethyl)-p-phenylenediamine sulphate | 0.6 g |
| 1,2,4-trihydroxybenzene | 0.25 g |
| Guar gum sold by the company Celanese under the name Jaguar HP60 | 1.0 g |
| Glycoside alkyl ether sold at a concentration of 60% AS by the company Seppic under the name Triton CG 110 | 5.0 g AS |
| Preservatives | 0.6 g |
| Monoethanolamine qs | pH 8 |
| Demineralized water qs | 100.0 g |

Three applications of this composition are carried out on natural grey hair containing 90% of white hair.

Each application corresponds to an exposure time of 10 minutes followed by a rinse, shampooing and drying. At the end, hair dyed in a dull golden dark blond hue is obtained, whereas three applications carried out under the same conditions with the composition containing only 2-methyl-5,6-dihydroxyindole hydrobromide lead to an ash-blond coloration, or containing only N,N-bis(2-hydroxyethyl)-p-phenylenediamine sulphate to an extremely light blond coloration, or containing only 1,2,4-trihydroxybenzene to a dull golden blond coloration.

EXAMPLE 5

| | |
|---|---|
| 5-Methoxy-6-hydroxyindole | 0.30 g |
| N,N-Bis(2-hydroxyethyl)-p-phenylenediamine sulphate | 0.45 g |
| Ethylene glycol monobutyl ether | 15.0 g |
| Sodium lauryl ether sulphate containing 2 moles of ethylene oxide, sold in solution containing 30% AS in water by the company Lever under the name Sactipon 8533 | 3.5 g AS |
| 2-Amino-2-methyl-1-propanol qs | pH 8.5 |
| Demineralized water qs | 100.0 g |

This composition is applied for 15 minutes on permanent-waved grey hair containing 90% of white hair. After rinsing and drying, a further three applications are performed. At the end, a pearly blond coloration is obtained, whereas four applications of each of the dyes in the same vehicle lead: in the case of N,N-bis(2-hydroxyethyl)-p-phenylenediamine sulphate to an extremely light blond coloration; and to no coloration in the case of 5-methoxy-6-hydroxyindole.

EXAMPLE 6

| | |
|---|---|
| 2-Methyl-N,N-dimethyl-p-phenylenediamine dihydrochloride | 0.3 g |
| 5,6-Dihydroxyindole | 0.3 g |
| Xanthan gum sold by the company Rhone Poulenc under the name Rhodopol SC | 2.0 g |
| Glycoside alkyl ether sold at a concentration of 60% AS by the company Seppic under the name Triton CG 110 | 2.1 g AS |
| Triethanolamine | 4.0 g |
| Tartaric acid | 0.3 g |
| Ethyl alcohol | 10.0 g |
| Preservative qs | |
| Water qs | 100.0 g |

Three applications of this composition are performed on permanent-waved grey hair containing 90% of white hair.

Each application corresponds to an exposure time of 10 minutes; it is followed by a rinse, shampooing and drying. The final coloration of the hair is a bluish black natural hue, whereas that obtained under the same conditions with 5,6-dihydroxindole alone is a medium grey, and 2-methyl-N,N-dimethyl-p-phenylenediamine dihydrochloride alone does not dye.

EXAMPLE 7

| | |
|---|---|
| 2-Chloro-N,N-dimethyl-p-phenylenediamine dihydrochloride | 0.3 g |
| 5,6-Dihydroxyindole | 0.3 g |
| Xanthan gum sold by the company Rhone Poulenc under the name Rhodopol SC | 2.0 g |
| Glycoside alkyl ether sold at a concentration of 60% AS by the company Seppic under the name Triton CG 110 | 2.1 g AS |
| Triethanolamine | 4.0 g |
| Tartaric acid | 0.3 g |
| Ethyl alcohol | 10.0 g |
| Preservative qs | |
| Water qs | 100.0 g |

Three applications of this composition are performed on permanent-waved grey hair containing 90% of white hair.

Each application corresponds to an exposure time of 10 minutes; it is followed by a rinse, shampooing and drying. The final coloration of the hair is a dark grey natural hue, whereas that obtained under the same conditions with 5,6-dihydroxyindole alone is a medium grey, and 2-chloro-N,N-dimethyl-p-phenylenediamine dihydrochloride alone does not dye.

EXAMPLE 8

| | |
|---|---|
| N-methyl-N-2-hydroxyethyl-3-methyl-p-phenylenediamine | 0.3 g |
| 5,6-dihydroxyindole | 0.3 g |
| Xanthan gum sold under the name of RHODOPOL SC by the Company RHONE POULENC | 2,0 g |
| glycoside alkyether sold at a concentration at 60% AS by the Company SEPPIC under the name TRITON CG 110 | 2,1 g AS |
| triethanolamine | 4,0 g |
| tartaric acid | 0,3 g |
| ethyl alcohol | 10,0 g |
| preservative qs | |
| water qs | 100,0 g |

Three applications of this composition are performed on permanent-waved grey hair containing 90% of white hair.

Each application corresponds to an exposure time of 10 minutes; it is followed by a rinse, shampooing and drying. The final coloration of the hair is a natural medium grey hue, whereas that obtained under the same conditions with 5,6-dihydroxyindole alone is a medium grey and N-methyl-N-2-hydroxyethyl-3-methyl-p-phenylenediamine alone does not dye.

I claim:

1. A composition for dyeing keratinous fibers comprising in a cosmetically acceptable aqueous medium
   (a) at least one indole dye having the formula

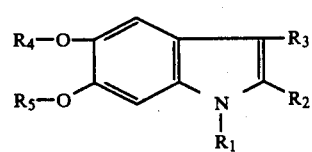

(I)

wherein
$R_1$ represents hydrogen, lower alkyl or $-SiR_6R_7R_8$.

$R_2$ and $R_3$, each independently, represent hydrogen, lower alkyl, carboxyl, lower alkoxy carbonyl or $-COOSiR_6R_7R_8$, $R_4$ and $R_5$, each independently, represent hydrogen, linear or branched $C_1-C_{20}$ alkyl, formyl, linear or branched $C_2-C_{20}$acyl, linear or branched $C_3-C_{20}$ alkenoyl, $-SiR_6R_7R_8$, $-P(O)(OR_9)_2$ or $-SO_2OR_9$, or $R_4$ and $R_5$ together with the oxygen atoms to which they are attached form a ring optionally containing a carbonyl group, a methylene group, a thiocarbonyl group, a $>P(O)OR_9$ group or a $>CR_{10}R_{11}$ group, $R_9$ and $R_{10}$ represent hydrogen or lower alkyl, $R_{11}$ represents lower alkoxy, monoalkylamino or dialkylamino, and $R_6$, $R_7$ and $R_8$, each independently, represent linear or branched alkyl, and the acid addition salt thereof with an inorganic or organic acid or the corresponding alkali metal, alkaline earth metal or amine salt thereof, said indole dye being present in an amount ranging from 0.1 to 5 percent by weight based on the total weight of said composition, and (b) a para-phenylenediamine disubstituted on one of the amino groups thereof and having the formula

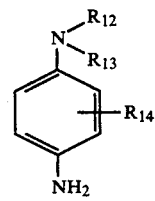

(II)

wherein
$R_{12}$ and $R_{13}$, each independently, represent $C_1-C_4$ alkyl, $C_2-C_4$ hydroxyalkyl, $C_1-C_4$ alkyl substituted with $SO_3H$, mesylamino, acetylamino, $C_1-C_4$ alkoxy, carbamyl or carbamyl substituted with one or two $C_1-C_4$ alkyl groups or with a heterocyclic amine, or $R_{12}$ and $R_{13}$ together with the nitrogen atom to which they are attached form a 4- to 6-membered heterocycle; and $R_{14}$ in position 2- or 3- represents hydrogen, $C_1-C_4$ alkyl, $C_1-C_4$ alkoxy or halogen, or the cosmetically acceptable salt thereof with an acid, said para-phenylenediamine being present in an amount ranging from 0.05 to 1 percent by weight based on the total weight of said composition.

2. The composition of claim 1 wherein in said para-phenylenediamine, $R_{12}$ and $R_{13}$, each independently, represent methyl, ethyl, hydroxyethyl, ethy substituted with mesylamino, acetylamino, $SO_3H$, methoxy, piperidine, or methyl substituted with carbamyl or diethylcarbamyl, and $R_{14}$ represents hydrogen or ethyl, or a salt thereof.

3. A composition for dyeing keratinous fibers comprising in a cosmetically acceptable aqueous medium
   (a) 5,6-dihydroxyindole present in an amount ranging from 0.1 to 5 percent by weight based on the total weight of said composition and
   (b) a para-phenylenediamine disubstituted on one of the amino groups thereof and having the formula

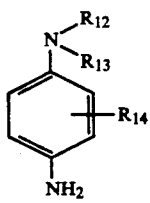

wherein $R_1$ and $R_2$, each independently, represent $C_1$-$C_4$ alkyl, $C_2$-$C_4$ hydroxyalkyl, $C_1$-$C_4$ alkyl substituted with $SO_3H$, mesylamino, acetylamino, $C_1$-$C_4$ alkoxy, carbamyl or carbamyl substituted with one or two $C_1$-$C_4$ alkyl groups, or a heterocyclic amine, or $R_1$ and $R_2$ together with the nitrogen atom to which they are attached form a 4- to 6-membered heterocycle; or a cosmetically acceptable acid addition salt thereof, said para-phenylenediamine being present in an amount ranging from 0.05 to 1 percent by weight based on the total weight of said composition.

4. The composition of claim 1 wherein said paraphenylenediamine is selected from the group consisting of N-ethyl-N-(2-hydroxyethyl) paraphenylenediamine, N-ethyl-N-(2-hydroxyethyl) paraphenylenediamine sulphate, N-ethyl-N-(2-hydroxyethyl) paraphenylenediamine hydrochloride, N,N-bis(2-hydroxyethyl) paraphenylenediamine or a salt thereof, N-ethyl-N-(2-piperidinoethyl) paraphenylenediamine or its trihydrochloride. N-ethyl-N-(carbamylmethyl) paraphenylenediamine, N-ethyl-N-[2-(mesylamino)ethyl]-paraphenylenediamine or its sulphate and 2-methyl-N,N-dimethyl-paraphenylenediamine or a salt thereof.

5. The composition of claim 1 wherein said indole is selected from the group consisting of 5,6-dihydroxyindole, 2-methyl-5,6-dihydroxyindole, 5-methoxy-6-hydroxyindole, 5-acetoxy-6-hydroxyindole, 6-acetoxy-5-hydroxyindole, a mixture of 5-acetoxy-6-hydroxyindole and 6-acetoxy-5-hydroxyindole, 2-carboxy-5,6-dihydroxyindole, 3-methyl-5,6-dihydroxyindole, 2,3-dimethyl-5,6-dihydroxyindole and a salt thereof.

6. The composition of claim 1 wherein said paraphenylenediamine is present in an amount ranging from 0.1 to 0.7 percent by weight based on the total weight of said composition.

7. The composition of claim 1 wherein said indole is present in an amount ranging from 0.2 to 2 percent by weight based on the total weight of said composition.

8. The composition of claim 16 wherein said trihydroxylated benzene is 1,2,4-trihydroxybenzene 1,2,4-trihydroxybenzene triacetate, 2,4,5-trihydroxytoluene or 2,4,5-trihydroxytoluene triacetate.

9. The composition of claim 16 wherein said trihydroxylated benzene is present in an amount ranging from 0.05 to 0.3 percent by weight based on the total weight by said composition.

10. The composition of claim 1 wherein said indole is 5,6-dihydroxyindole and said paraphenylenediamine is N,N-bis(2-hydroxyethyl) paraphenylenediamine, and said composition also includes 1,2,4-trihydroxybenzene or the acetate thereof.

11. The composition of claim 1 having a pH ranging from 4 to 11.

12. The composition of claim 1 wherein said aqueous medium contains up to 30 weight percent of a solvent selected from an alcohol, a glycol, a glycol ether, ethylene glycol monoethyl ether acetate or methyl lactate.

13. The composition of claim 1 in the form of a thickened lotion, an unthickened lotion, a gel or an aerosol foam.

14. The process of claim 15 which includes several successive applications of said composition to said fibers so as to obtain an increasingly dark tinting of said fibers.

15. A process for dyeing keratinous fibers comprising applying to said fibers a fiber dyeing amount of a composition comprising
   (a) at least one indole dye having the formula

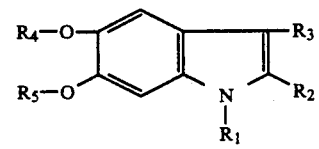

wherein $R_1$ represents hydrogen, lower alkyl or $-SiR_6R_7R_8$.

$R_2$ and $R_3$, each independently, represent hydrogen, lower alkyl, carboxyl, lower alkoxy carbonyl or $-COOSiR_6R_7R_8$, $R_4$ and $R_5$, each independently, represent hydrogen, linear or branched $C_1$-$C_{20}$ alkyl, formul, linear or branched $C_2$-$C_{20}$ acyl, linear or branched $C_3$-$C_{20}$ alkenoyl, $-SiR_6R_7R_8$, $-P(O)(OR_9)_2$ or $-SO_2OR_4$ or $R_4$ and $R_5$ together with the oxygen atoms to which they are attached form a ring optionally containing a carbonyl group, a methylene group, a thiocarbonyl group, a $>P(O)OR_9$ group or a $>CR_{10}R_{11}$ group, $R_9$ and $R_{10}$ represent hydrogen or lower alkyl, $R_{11}$ represents lower alkoxy, monoalkylamino or dialkylamino, and $R_6$, $R_7$ and $R_8$, each independently, represent linear or branched alkyl, or the acid addition salt thereof with an inorganic or organic acid or the corresponding alkali metal, alkaline earth metal or amine salt thereof, said indole dye being present in an amount ranging from 0.1 to 5 percent by weight based on the total weight of said composition, and (b) a para-phenylenediamine disubstituted on one of the amino groups thereof and having the formula

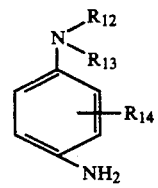

wherein $R_{12}$ and $R_{13}$, each independently, represent $C_1$-$C_4$ alkyl, $C_2$-$C_4$ hydroxyalkyl, $C_1$-$C_4$ alkyl substituted with $SO_3H$, mesylamino, acetylamino, $C_1$-$C_4$ alkoxy, carbamyl or carbamyl substituted with one or two $C_1$-$C_4$ alkyl groups or with a heterocyclic amine, or $R_{12}$ and $R_{13}$ together with the nitrogen atom to which they are attached form a 4- to 6-membered heterocycle; and $R_{14}$ in position 2- or 3- represents hydrogen, $C_1$-$C_4$ alkyl, $C_1$-$C_4$ alkoxy or halogen, or the cosmetically acceptable salt thereof with an acid, said para-phenylenediamine being present in an amount ranging from 0.05 to 1 percent by weight based on the total weight of said composition and, permitting said composition to remain in contact with said fibers for a period of time sufficient for a color to develop on said fibers.

16. A composition for dyeing keratinous fibers comprising in a cosmetically acceptable aqueous medium
(a) at least one indole dye having the formula

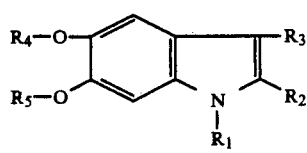

(I)

wherein $R_1$ represents hydrogen, lower alkyl or —$SiR_6R_7R_8$, $R_2$ and $R_3$, each independently, represent hydrogen, lower alkyl, carboxyl, lower alkoxy carbonyl or —$COOSiR_6R_7R_8$, $R_4$ and $R_5$, each independently, represent hydrogen, linear or branched $C_1$-$C_{20}$ alkyl, formyl, linear or branched $C_2$-$C_{20}$ acyl, linear or branched $C_3$-$C_{20}$ alkenoyl, —$SiR_6R_7R_8$, —$P(O)(OR_9)_2$ or —$SO_2OR_9$, or $R_4$ and $R_5$ together with the oxygen atoms to which they are attached form a ring optionally containing a carbonyl group, a methylene group, a thiocarbonyl group, a >$P(O)OR_9$ group or a >$CR_{10}R_{11}$ group, $R_9$ and $R_{10}$ represent hydrogen or lower alkyl, $R_{11}$ represents lower alkoxy, monoalkylamino or dialkylamino, and $R_6$, $R_7$ and $R_8$, each independently, represent linear or branched alkyl, and the acid addition salt thereof with an inorganic or organic acid or the corresponding alkali metal, alkaline earth metal or amine salt thereof, said indole dye being present in an amount ranging from 0.1 to 5 percent by weight based on the total weight of said composition, (b) a paraphenylenediamine disubstituted on one of the amino groups thereof and having the formula

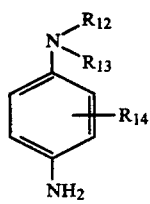

(II)

wherein $R_{12}$ and $R_{13}$, each independently, represent $C_1$-$C_4$ alkyl, $C_2$-$C_4$ hydroxyalkyl, $C_1$-$C_4$ alkyl substituted with $SO_3H$, mesylamino, acetylamino, $C_1$-$C_4$ alkoxy, carbamyl or carbamyl substituted with one or two $C_1$-$C_4$ alkyl groups or with a heterocyclic amine, or $R_{12}$ and $R_{13}$ together with the nitrogen atom to which they are attached form a 4- to 6-membered heterocycle; and $R_{14}$ in position 2- or 3- represents hydrogen, $C_1$-$C_4$ alkyl, $C_1$-$C_4$ alkoxy or halogen, or the cosmetically acceptable acid addition salt thereof, said paraphenylenediamine being present in an amount ranging from 0.05 to 1 percent by weight based on the total weight of said composition, and (c) at least one trihydroxylated benzene present in an amount ranging from 0.02 to 1 percent by weight based on the total weight of said composition.

17. A process for dyeing keratinous fibers comprising applying to said fibers a fiber dyeing amount of a composition comprising in a cosmetically acceptable aqueous medium
(a) at least one indole dye having the formula

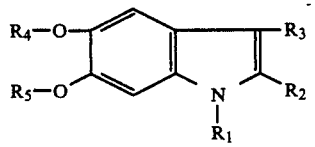

(I)

wherein $R_1$ represents hydrogen, lower alkyl or —$SiR_6R_7R_8$, $R_2$ and $R_3$, each independently, represent hydrogen, lower alkyl, carboxyl, lower alkoxy carbonyl or —$COOSiR_6R_7R_8$, $R_4$ and $R_5$, each independently, represent hydrogen, linear or branched $C_1$-$C_{20}$ alkyl, formyl, linear or branched $C_2$-$C_{20}$ acyl, linear branched $C_3$-$C_{20}$ alkenoyl, —$SiR_6R_7R_8$, —$P(O)(OR_9)_2$ or —$SO_2OR_9$, or $R_4$ and $R_5$ together with the oxygen atoms to which they are attached form a ring optically containing a carbonyl group, a methylene group, a thiocarbonyl group, a >$P(O)OR_9$ group or a >$CR_{10}R_{11}$ group, $R_9$ and $R_{10}$ represent hydrogen or lower alkyl, $R_{11}$ represents lower alkoxy, monoalkylamino or dialkylamino, and $R_6$, $R_7$ and $R_8$, each independently, represent linear or branched alkyl, and the acid addition salt thereof with an inorganic or organic acid or the corresponding alkali metal, alkaline earth metal or amine salt thereof, said indole dye being present in an amount ranging from 0.1 to 5 percent by weight based on the total weight of said composition, (b) a paraphenylenediamine disubstituted on one of the amino groups thereof and having the formula

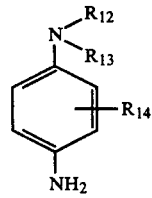

(II)

wherein $R_{12}$ and $R_{13}$, each independently, represent $C_1$-$C_4$ alkyl, $C_2$-$C_4$ hydroxyalkyl, $C_1$-$C_4$ alkyl substituted with $SO_3H$ mesylamino, acetylamino, $C_1$-$C_4$ alkoxy, carbamyl or carbamyl substituted with one or two $C_1$-$C_4$ alkyl groups or with a heterocyclic amine, or $R_{12}$ and $R_{13}$ together with the nitrogen atom to which they are attached form a 4- or 6- membered heterocycle; and $R_{14}$ in position 2- or 3- represents hydrogen, $C_1$-$C_4$ alkyl, $C_1$-$C_4$ alkoxy or halogen, or the cosmetically acceptable acid addition salt thereof, said paraphenylenediamine being present in an amount ranging from 0.05 to 1 percent by weight based on the total weight of said composition, and (c) at least one trihydroxylated benzene present in an amount ranging from 0.02 to 1 percent by weight based on the total weight of said composition and, permitting said composition to remain in contact with said fibers for a period of time sufficient for a color to develop on said fibers.

* * * * *